US010143633B2

(12) United States Patent
Kutsch

(10) Patent No.: US 10,143,633 B2
(45) Date of Patent: Dec. 4, 2018

(54) TREATING CARIOGENIC DISEASED ORAL BIOFILM WITH ELEVATED PH

(71) Applicant: Dental Alliance Holdings, LLC, Albany, OR (US)

(72) Inventor: V. Kim Kutsch, Albany, OR (US)

(73) Assignee: DENTAL ALLIANCE HOLDINGS, LLC, Albany, OR (US)

( * ) Notice: Subject to any disclaimer, the term of this patent is extended or adjusted under 35 U.S.C. 154(b) by 349 days.

(21) Appl. No.: 14/677,927

(22) Filed: Apr. 2, 2015

(65) Prior Publication Data

US 2015/0305992 A1 Oct. 29, 2015
US 2016/0374909 A9 Dec. 29, 2016

Related U.S. Application Data

(63) Continuation of application No. 11/973,843, filed on Oct. 10, 2007.

(60) Provisional application No. 60/852,167, filed on Oct. 16, 2006.

(51) Int. Cl.
A61K 8/21 (2006.01)
A61K 8/20 (2006.01)
A61K 33/14 (2006.01)
A61Q 11/00 (2006.01)
A61Q 11/02 (2006.01)

(52) U.S. Cl.
CPC ............... *A61K 8/21* (2013.01); *A61K 8/20* (2013.01); *A61Q 11/00* (2013.01); *A61K 2800/85* (2013.01)

(58) Field of Classification Search
CPC ........ A61K 8/21; A61K 8/20; A61K 2800/85; A61Q 11/02; A61Q 11/00
See application file for complete search history.

(56) References Cited

U.S. PATENT DOCUMENTS

| | | | |
|---|---|---|---|
| 4,150,151 A | 4/1979 | Pader et al. | |
| 4,372,978 A | 2/1983 | Gilbertson et al. | |
| RE31,815 E | 1/1985 | Alfano | |
| 5,089,255 A * | 2/1992 | Gaffar | A61K 8/21 424/52 |
| 5,213,615 A | 5/1993 | Michl | |
| 5,607,672 A | 3/1997 | Hillman | |
| 5,738,113 A | 4/1998 | Connelly | |
| 5,770,182 A | 6/1998 | Fischer | |
| 5,804,165 A | 9/1998 | Arnold | |
| 6,043,047 A | 3/2000 | Foote et al. | |
| 6,314,960 B1 | 11/2001 | Vines | |
| 6,342,207 B1 | 1/2002 | Stoor et al. | |
| 6,375,934 B1 | 4/2002 | Eklund et al. | |
| 6,484,144 B2 | 11/2002 | Martin et al. | |
| 6,548,018 B2 | 4/2003 | DiCasare et al. | |
| 6,685,921 B2 | 2/2004 | Lawlor | |
| 6,846,478 B1 | 1/2005 | Doyle et al. | |
| 2002/0114768 A1 | 8/2002 | Stoor et al. | |
| 2002/0114851 A1 * | 8/2002 | Camper | A61K 8/20 424/665 |
| 2003/0205234 A1 | 11/2003 | Bardach et al. | |
| 2005/0025720 A1 | 2/2005 | Bailey | |
| 2005/0100866 A1 | 5/2005 | Arnone et al. | |
| 2005/0142074 A1 | 6/2005 | Pushpangadan et al. | |
| 2005/0169852 A1 | 8/2005 | Roberge et al. | |
| 2005/0191247 A1 | 9/2005 | Drake et al. | |
| 2008/0057531 A1 | 3/2008 | Machida et al. | |

FOREIGN PATENT DOCUMENTS

CA 986022 3/1976
JP 10-330234 12/1998

OTHER PUBLICATIONS

Niosh ("Sodium Hypochlorite (Solution, Active Chlorine > 5%)". International Chemical Safety Cards. https://web.archive.org/web/19990903080400/http://www.cdc.gov/NIOSH/ipcsneng/neng1119.html. Sep. 3, 1999. 2 pages.).*
U.S. Appl. No. 12/456,849, Aug. 31, 2011, Kutsch Office Action.
U.S. Appl. No. 12/456,849, Jan. 23, 2013, Kutsch Office Action.
U.S. Appl. No. 12/456,849, Apr. 6, 2016, Kutsch Office Action.
U.S. Appl. No. 12/456,849, Sep. 14, 2016, Kutsch Office Action.
U.S. Appl. No. 11/973,843, Sep. 16, 2011, Kutsch Office Action.
U.S. Appl. No. 11/973,843, Nov. 26, 2012, Kutsch Office Action.
U.S. Appl. No. 11/973,843, Oct. 7, 2013, Kutsch Office Action.
U.S. Appl. No. 11/337,435, Apr. 17, 2015, Kutsch Office Action.
U.S. Appl. No. 11/337,435, May 30, 2014, Kutsch Office Action.
U.S. Appl. No. 11/337,435, Oct. 15, 2015, Kutsch Office Action.
U.S. Appl. No. 11/337,435, Jan. 5, 2016, Kutsch Office Action.
U.S. Appl. No. 13/080,644, Nov. 21, 2012, Kutsch Office Action.
U.S. Appl. No. 13/080,644, Oct. 3, 2014, Kutsch Office Action.
U.S. Appl. No. 13/080,644, May 8, 2015, Kutsch Office Action.
Kutsch-Renyer Newsletter Fall/Winter 2005, Albany, OR 97321, patient newsletter, see p. 1 for relevant information.
Kutsch, VK: CAMBRA: Caries Management by Risk Assessment, Part 1 Oregon/SW Washington Doctor of Dentistry. Jan. 2004.
Kutsch, VK: How to Integrate CAMBRA into a Dental Practice, Part II, Oregon/SW Washington Doctor of Dentistry, Feb. 2004.
Steimke. A, Dtsch zahnarztL z.38, 918-920 (1983) (Englsih abstract is on p. 920) in German.
www.kpchr.org/publicldental/mission.htm Mission Statement, Oral Health Research Progrrn (no named author), 2003.
Spaeth, Dennis, Not your father's dentistry, Dental Practice Report, JUUAUG2003.
Rethman, Jill, Trends in Preventive Care Caries Risk Assessment and Indications for Sealants, JADA, vol. 131, Jun. 2002.
Search printout from Google, Feb. 21, 2004 frOm searching Kutsch and Chicago Il Midwinter (six pge search pintout, no author).
Davidson et al, Evaluation of two methods of monitoring surface cleanliness—ATP bioluminescence and traditional hygiene swabbing, Luminescence 1999.

(Continued)

*Primary Examiner* — Jeffrey S Lundgren
*Assistant Examiner* — Chris E Simmons
(74) *Attorney, Agent, or Firm* — John Connors; Connors & Assoc. pc

(57) ABSTRACT

A method of treating biofilm disease using a pH adjusted therapeutic rinse that comprises two parts that are separated and in amounts that upon mixing provide a single dose. The two parts together and then rinsing a patient's mouth with the single dose and expectorating.

4 Claims, 1 Drawing Sheet

(56) References Cited

OTHER PUBLICATIONS

Featherstone et al, Caries Management by Risk Assessment: Consensus Statement, Apr. 2002, CDC Journal—Feature Article, Mar. 2003 Journal of Calif. Dental Assoc.
Robrish, Use of Extractable Adenosine Triphosphate to Estimate the Viable Cell Mass in Dental Plaque Samples Obtained From Monkeys, American Society of Microbiology, Apr. 1978.

\* cited by examiner

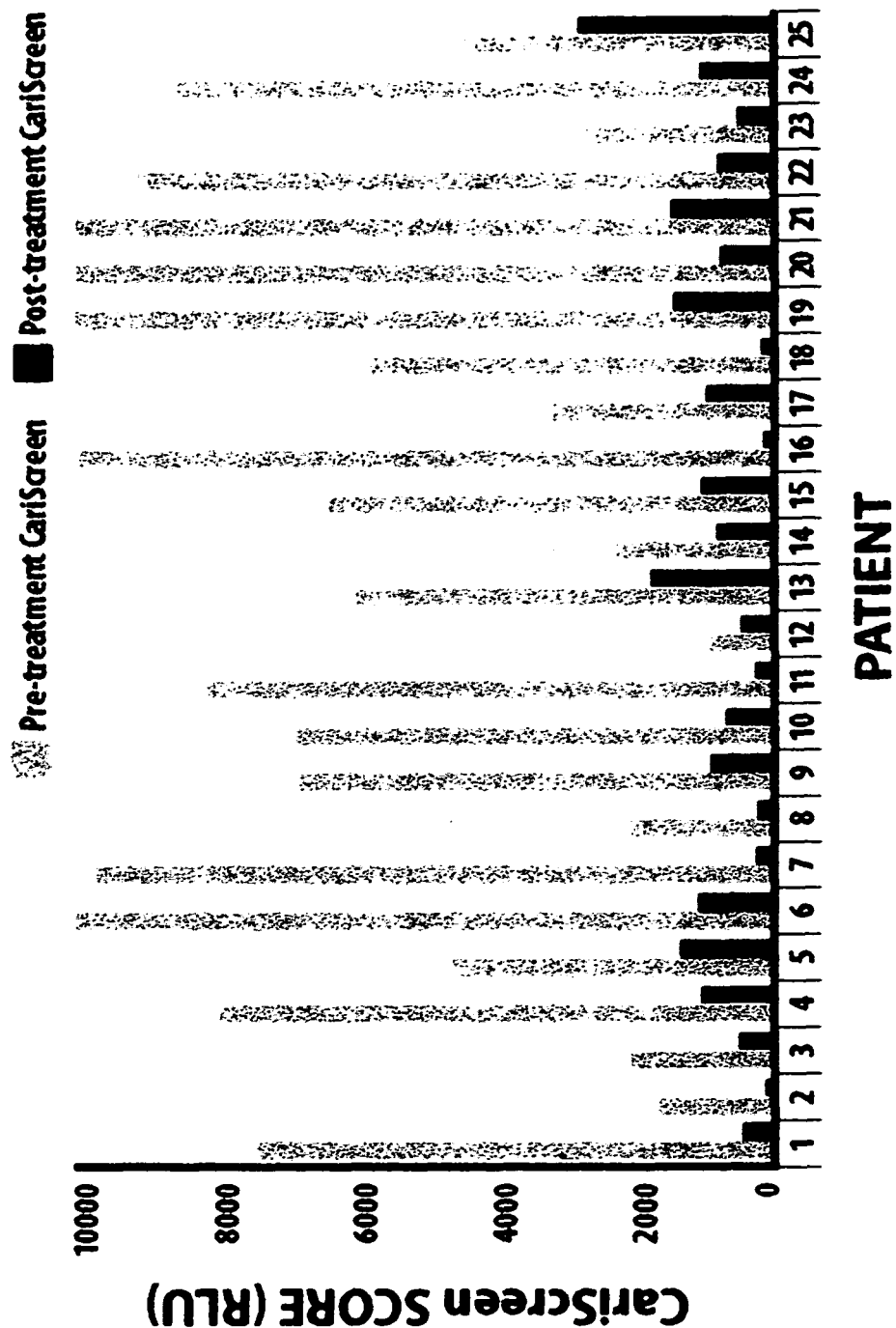

TREATING CARIOGENIC DISEASED ORAL BIOFILM WITH ELEVATED PH

RELATED PATENT APPLICATIONS & INCORPORATION BY REFERENCE

This utility application is a continuation application of U.S. application Ser. No. 11/973,843, entitled "TREATING CARIOGENIC DISEASED ORAL BIOFILM WITH ELEVATED pH OR pH BUFFERING ORAL HEALTH CARE PRODUCTS," filed Oct. 10, 2007, which claims priority of U.S. provisional application 60/852,167, filed Oct. 16, 2006. This related applications are incorporated herein by reference and made a part of this application. Moreover, any and all U.S. patents, U.S. patent applications, and other documents, hard copy or electronic, cited or referred to in this application are incorporated herein by reference and made a part of this application.

1. Field of the Invention

The present invention relates to treating a dental patient's oral health, such as cavities, as symptoms of a biofilm disease. The invention describes and claims treatment of the disease with high-pH or pH buffering health care products.

2. Background and Related Art

Oral health problems such as cavities result from a biofilm disease. In the past dentists generally only treated the symptoms, i.e. filling cavities, and not the cause of the symptoms, so patients continued to get cavities.

Others have tried to solve this problem in the past with antimicrobial agents including rinses, toothpastes, gels, gums, and other oral health care products that are acidic in pH. The problem is that the diseased biofilm in the mouth contains >96% acidogenic and aciduric bacteria. These bacteria are unique in their ability to maintain intra-cellular neutrality in an acidic biofilm because they have an H+ ion pump mechanism that allows them to continuously pump the acidic ions out of their cells and into the biofilm.

The pH of the biofilm in the mouth is acidic and results in the chemical dissolution of the calcium salts from tooth enamel which ultimately results in a cavity. The healthy and desirable oral bacteria cannot survive in an acidic environment, so treating the biofilm with an acidic product, drives the pH of the biofilm lower. Lower pH is moving in the wrong direction for the proper pH in maintaining dental health.

Applicants have discovered that three things that are effective against a bacterial oral biofilm are 1) heat, 2) mechanical debridement, and 3) a strong oxidizing agent. The present invention provides antimicrobial and remineralization oral health care products with a pH that is alkaline (higher pH) rather than acidic (lower pH) and also contains pH buffering agents. These higher pH agents drive the pH of the biofilm to the correct, higher level for healthy bacteria to reform in the oral biofilm and prevent cavities. The oral care antimicrobial/remineralization products of this invention have a pH that ranges between 8.0-11.5. The oral health care products of this invention include rinses, oral sprays, toothpastes, gels, varnishes, creams, gums, mints, floss, toothpicks, swabs, brushes, sponges, and dissolving strips.

Earlier antimicrobial/remineralization products such as described in U.S. Pat. No. 4,367,218 were either remineralization products that contain fluoride or calcium salts, which usually are of an acidic pH. Antimicrobial products are also mostly all acidic in pH. Another category of product had an elevated pH include a rinse based on sodium bicarbonate and aluminum salts, with a pH up to 9.4. This rinse was not an antimicrobial or remineralization product.

Additional work by others has been done on controlling the level of bacteria in the mouth. In U.S. Pat. No. 7,060,726 Hiramoto et al described using a mixture of coumarin analogues obtained from citrus fruit products. Leusch et al, in U.S. Pat. No. 6,238,648 disclose oral care compositions that combine a non-cariogenic carbohydrate and polyalcohol. Kramer et al., in U.S. Pat. No. 6,290,934 disclose agents for the promotion of oral health comprising ionically bound or free thiocyanate ions and carbamide perhydrate in combination with known additives and vehicles.

Other patents of interest to applicants include Lee et al in U.S. Pat. Nos. 6,214,321 and 6,120,754. The Lee works deal with the remineralization of teeth. Both patents teach first and second compositions, the first composition having a pH less than 7 and the second composition having a pH greater than 7. When combined upon application to teeth, the first and second compositions generate hydroxyapatite depositing same on dental enamel. Lee's elevated pH is quite different from applicants' invention wherein higher pH is desired in and of itself to raise the pH of dental biofilm.

High pH is mentioned in U.S. Pat. No. 6,872,565 by Mollstam et al. Mollstam is concerned with reducing the number of *Streptococcus mutans* in the mouth through inhibiting activity in combination with good binding to the oral mucins and dental plaque. A high pH material is used in at least one example.

A bioengineered bacterial organism to over express two or more *Lactococcus lactis* HtrA to promote the inhibition or removal of a biofilm is presented by Wang et al in US Patent Publication 2007/0059295. Applicants have no such organism.

In U.S. Pat. No. 5,603,920 Rice discloses a dentifrice composition wherein the pH is above 9. In his invention, Rice does not mention the oral biofilm at all.

SUMMARY OF THE INVENTION

The present invention provides antimicrobial and remineralization oral health care products with higher, alkaline pH and pH buffers. These products drive the pH of the biofilm to the correct level for the healthy bacteria to reform in the biofilm and prevent cavities. Among the oral health care products are rinses, oral sprays, toothpastes, gels, varnishes, creams, gums, mints, floss, toothpicks, swabs, brushes, sponges, and dissolving strips and the like. Methods of using these products are also described and claimed herein.

DEFINITIONS USED IN THIS INVENTION

In this invention, 'acidogenic' bacteria will mean acid-forming bacteria. In this invention, 'aciduric' will mean relating to bacteria that tolerate an acid environment.

In this invention, low pH will mean pH values that are lower than 7.

In this invention, high pH will mean pH values that are higher than 7.

In this invention, biofilm is a complex aggregation of microorganisms marked by the excretion of a protective and adhesive matrix. A typical biofilm of this invention is the dental plaque that forms on teeth that causes tooth decay and is a bacterial biofilm.

DETAILED DESCRIPTION OF PREFERRED EMBODIMENTS

Applicants have developed oral care products including several oral rinses that are pending in a current U.S. patent application Ser. No. 11/337,435 filed on Jan. 23, 2005 and entitled "System for Caries Management by Risk Assessment". The rinses described therein are antimicrobial/remineralization with pH values of about 8.0 and 11.50. The pH values ranging between 10 and 11.5 are about as strong as patients can tolerate without the burning of the oral soft tissue.

For the purposes of the present patent application, a plurality of the available oral care products on the market was tested for pH. As seen in Table 1, it was discovered that they were virtually all acidic in pH; some with a pH as low as 4.04.

Dental caries is now defined by the dental profession as a biofilm disease, with the caries causing bacteria taking control of the biofilm on the teeth. When the oral environment favors these bacteria, the biofilm population shifts from the normal healthy flora to the acidogenic and aciduric bacteria associated with dental caries. As more is learned about controlling the oral biofilm, the three things listed supra are known to be effective against biofilms in general. Because of the structure and function of biofilms, they are only susceptible to complete debridement, heat, and strong oxidizing agents. In the mouth, it is nearly impossible to completely debride the cariogenic biofilm away. The biofilm reforms within hours after it is removed and bacteria are ubiquitous in the mouth. Heat is not a good option, as heat that is applied to the oral structures at a high enough temperature to destroy the bacteria, would also destroy the host tissues. Strong oxidizing agents offer some potential as antimicrobial agents in safe-to-use concentrations.

ATP bioluminescence has been used for over 40 years to rapidly identify the bacterial load of an environment. ATP is the energy molecule used by all living cells, and if it is present in water or on a surface, the ATP present is indicative of the bacterial load. When the ATP sample is mixed with stabilized luciferin/luciferinase, it emits light and can be measured in a light sensitive meter. ATP bioluminescence is a non-specific test, as specific bacterial species cannot be identified. In the mouth, there is also an unknown amount of human somatic ATP levels, depending upon the recent activity of the mouth.

There is a strong direct correlation between the ATP bioluminescence level of the oral biofilm in a mouth at rest, and the number of Cariogenic bacteria present. During three separate randomized clinical trials, it was determined that there was a strong direct correlation between the Caries Susceptibility Test score and the number of colony forming units (CFUs) of *Mutans streptococci*, a known cariogenic bacteria strain. The graph of twenty-five patients and their pre and post treatment CariScreen Scores is shown in FIG. 1.

As seen from the big difference in the heights of the bars for each patient, treatment with a product of this invention greatly reduced the RLU (relative light units, labeled "Cariscreen®")) scores for patients after treatment. As noted above, the amount of *Mutans streptococci* in these patients is greatly reduced.

Fluoride reduces the acid solubility of enamel, and reduces the pH demineralization threshold from 5.5 to 4.5. It also affects the metabolism of cariogenic bacteria. Fluoride has been applied systemically in water supplies and by prescription tablets, and topically with fluoride toothpaste, fluoride rinses, gels and foams. It is also applied directly to the teeth in varnishes. Other attempts at antimicrobial therapy have focused mainly around the use of chlorhexidine in either a rinse or a varnish. While chlorhexidine is effective against *Mutans streptococci*, it has no effect against Lactobacilli and the effect on other cariogenic bacteria is not known. Xylitol is known to disrupt the metabolism of *Mutans streptococci* and other cariogenic bacteria. These bacteria readily ingest the xylitol, but are unable to digest it and must expend additional energy to expel it from the cell.

Xylitol has been used in rinses, toothpastes and gels, mints, gum and assorted other products. With lack of an effective antimicrobial product, some researchers and clinicians have even used Betadine®, 10% Povidone Iodine as a mouth rinse. The problem with Betadine, aside from the unpleasant taste, is the fact that it can only be used one time per month because the iodine/thyroid interaction. A significant number of people who are allergic to shellfish are also allergic to iodine.

The elevated pH and pH buffering capability of the products of the instant invention plays a major role in the reestablishment of a healthy, normal biofilm. The cariogenic biofilm is acidogenic and aciduric, and the pH of the biofilm is acidic, favoring these bacteria. One important consideration in treatment is to drive the pH of the biofilm up to basic levels, giving the healthy bacteria a better opportunity to reestablish a healthy, protective biofilm on the teeth.

The advantages of applicants' solution over previous solutions is that the currently described group of products are simple and effective antimicrobial remineralization oral health care products with an elevated pH and pH buffers that drives the pH of the oral biofilm above at least a value of 7.0. This serves to greatly reduce and/or eliminate the acidogenic/aciduric bacteria that cause dental caries. It also favors the healthy bacteria that protect the teeth in a healthy biofilm with elevated pH values.

The prior art of U.S. Pat. No. 4,367,218 requires the metallic carbonate/bicarbonate salts of their product rinses to be shaken and then rinsed in the mouth every 30 minutes throughout the day. The products of the present invention do not require shaking, and they only need to be used one or two times per day on the same schedule that a patient uses normal oral care products such as mouthwash, floss, toothpaste and the like.

Applicants' solution would not be obvious to other inventors in the dental field because dentistry has been focused on producing acidic products and have not done experiments with highly elevated pH products to determine treatment outcomes. The present invention runs contrary to the beliefs and procedures for current dental health and products supporting dental well-being. Applicants' solution to dental health problems is not intuitive and it is not obvious, as it is contrary to long-held tenets of dentistry.

Examples

Applicants have developed oral rinses that are antimicrobial and that help remineralization of the teeth with pH values ranging from 8.0 to 11.5, as well as pH buffering agents. The instant patent application encompasses many oral health care products such as toothpastes, gels, oral sprays, gum, mints, varnishes, floss, toothpicks, swabs, brushes, sponges, and dissolving strips.

Applicants have tested a large sampling of the available oral care products currently on the market for pH value which are shown in Table 1, below. The products were tested using a Beckman® 240 pH meter with a measurable pH range of 0-16 and FUTURA™ Gel-Filled Epoxy pH Electrode. After calibration with Chem Products color coded pH buffers, 3 separate pH readings were taken for each product and the average of the 3 readings was taken as final pH value. Virtually all of them tested acidic in pH. In fact, one product had a pH values as low as 4.04

TABLE 1

| Rinse Name | Tested pH |
| --- | --- |
| CariFree Treatment Rinse | 10.38 |
| CariFree Maintenance Rinse | 8.00 |
| Cepacol | 7.53 |
| Act | 6.36 |
| NeutraFlor 220 | 6.03 |
| NeutraFlor 900 | 5.98 |
| Colgate Fluorigard | 5.98 |
| Rembrandt Whitening | 5.73 |
| Listerine Whitening | 5.60 |
| Peridex | 5.50 |
| Scope | 5.45 |
| BreathRx | 4.77 |
| Oral-B Anticavity Rinse | 4.73 |
| Biotene Mouthwash | 4.67 |
| Oral-B Antibacterial Rinse | 4.65 |
| Listerine | 4.45 |
| BreathRx Antibacterial Mouth Spray | 4.35 |
| FluoroCare 200 | 4.31 |
| Crest Pro-Health | 4.24 |
| Tom's of Maine Natural Mouthwash | 4.04 |

The products of this invention are effective antimicrobial and remineralization oral health care products with an elevated pH and pH buffers. The elevated pH and ph buffers drive the pH of a patient's biofilm to an elevated level that will eliminate the acidogenic and aciduric bacteria that cause dental caries, and favors the healthy bacteria that protect the teeth in a healthy biofilm.

The following FIGURE, FIG. 1 shows the significant effect of the use of various products of this invention in terms of reduction of RLU post treatment with said products.

The FIGURE shows the large difference between the heights of the bars for 25 patients. It shows a significant decrease and improvement in RLU scores for each patient who has successfully completed a treatment with one product of the instant invention. There is a strong direct correlation between the ATP bioluminescence level of the oral biofilm in a mouth at rest, and the number of Cariogenic bacteria present. During three separate randomized clinical trials, it was determined that there was a strong direct correlation between the Caries Susceptibility Test score and the colony forming units (CFUs) of *Mutans streptococci*, a known cariogenic bacteria strain.

Product Summary

The products of this invention are designed to provide antimicrobial and remineralization oral health of a dental patient. As has been discussed, the products have a pH that is alkaline ranging from values of about 8.0 to about 11.5, as well as pH buffers. The alkalinity and buffers drive the pH of the biofilm in a patient's mouth to a level which encourages the growth of healthy bacteria that reforms the biofilm and improves the health of the patient's mouth. The instant invention comprises oral health care products selected from the group consisting of rinses including a maintenance rinse, a two-component treatment rinse, oral sprays, toothpastes, gels, varnishes, creams, chewing gums, mints, floss, toothpicks, swabs, brushes, sponges, and dissolving strips.

The rinses of this invention include both a maintenance rinse and a two part therapeutic rinse. The maintenance rinse comprises about 73 weight percent water, about 25 percent xylitol, about 1 weight percent sodium benzoate, about 1 percent potassium sorbate, 0.05 percent sodium fluoride, 0.2 percent citrus or mint flavor, 0.2 percent polysorbate 20, sodium bicarbonate, calcium hydroxide, or sodium hydroxide to boost and buffer pH to above 8.0, and trace amounts of 90% polyphenol and cranberry extract.

The therapeutic rinse of this invention is a two-part rinse that is utilized for two weeks and then is followed by a maintenance rinse. The treatment rinse contains fluoride as an active ingredient, along with a strong oxidizing agent selected from the group consisting of sodium hypochlorite, calcium hypochlorite, potassium hypochlorite, magnesium hypochlorite, and sodium hydroxide to buffer the treatment rinse to an elevated pH of 10.38-11.50. A single dose of this two part rinse is mixed each time it is used.

The two part treatment rinse includes the first part of the treatment rinse that comprises water in the amount of about 73 weight percent, xylitol in the amount of 22 weight percent, sodium benzoate in the amount of 2.0 weight percent, sodium fluoride in the amount of 0.05 weight percent, mint oil in the amount of 1.0 weight percent, poloxamer in the amount of 1.25 weigh percent, menthol in the amount of 1.0 weight percent, and the second part comprises water in the amount of about 92 weight percent, sodium hydroxide in a quantity to bring the pH of the second component to 11.9, and 5% sodium hypochlorite solution in the amount of 8 percent to bring the total sodium hypochlorite concentration to 0.4 percent.

The patient swishes the rinse in his mouth for a minute and then expectorates. After two weeks of the treatment rinse, the patient is then placed on daily use of the maintenance rinse. This single part rinse contains fluoride as the active ingredient, xylitol, an elevated pH of at least 8.0, a ph buffer, and the known naturally occurring antimicrobials polyphenol and anthocyanidins.

In addition to the antimicrobial basis for the rinses, they also have remineralization properties with the fluoride, and the elevated pH and pH buffers play a major role in the re-establishment of a healthy, normal biofilm. The cariogenic biofilm is acidogenic and aciduric, and the pH of the biofilm is acidic, favoring these bacteria. One important consideration in treatment is to drive the pH of the biofilm to basic levels, giving the healthy bacteria a better opportunity to reestablish a healthy, protective biofilm on the teeth. One concern about anti-caries rinses and products should be their pH. It does not make sense to treat and acidic biofilm with an acidic product, if the desired bacteria require an environment with neutral or basic pH.

Another product of this invention is an oral spray. The spray product allows patents to maintain the alkaline pH of their biofilm quickly and easily. Propylene glycol, polyethylene glycol, hydrogenated castor oil, aloe vera, sunflower oil, avocado oil, glycerin or flax seed oil can be optionally added in quantities less than 10% to increase oral moisturization.

Another product of this invention is a fluoride-free maintenance rinse. The fluoride-free maintenance rinse comprises about 72 weight percent water, about 15 weight percent xylitol, about 10 weight percent of one or more components selected from the group consisting of polyethylene glycol, hydrogenated castor oil, aloe vera, sunflower oil, avocado oil, glycerin and flax seed oil, about 0.2 weight percent sodium benzoate, about 1.8 weight percent potassium sorbate, traces of natural color and natural flavor and sodium hydroxide in an amount that buffers the pH of the rinse to a value between 8 and 10.

Another product of this invention is an oral gel that comprises water in the amount of about 68 weight percent, xylitol in the amount of 25 weight percent, hydroxyethyl cellulose in the amount of 1.65 weight percent, sodium benzoate in the amount of 0.1 weight percent, potassium sorbate in the amount of 1 weight percent, propylene glycol, glycerin, or polyethylene glycol in the amount of 10 weight percent, hydrogenated starch hydrolysate in the amount of 2 weight percent, sodium laurel sulfate in the amount of 1.2 weight percent, flavor in the amount of 1.1 weight percent, polysorbate 20 in the amount of 2 weight percent, calcium acetate in the amount of 0.01 weight percent, and sodium bicarbonate in the amount sufficient to buffer the composition to a pH value of at least 8. Sodium Fluoride may also be added to this product in the amount of 0.05-1.1 weight percent.

Another gel that is part of this invention is an oral gel comprising an aqueous solution of sorbitol 70% in the amount of 42 weight percent, distilled water in the amount of 20 weight percent, calcium carbonate in the amount of 10 weight percent, sodium bicarbonate in the amount of 5 weight percent, sodium laurel sulfate in the amount of 2 weight percent, titanium dioxide in the amount of 1 weight percent, precipitated silica in the form of Zeodent® 113 in the amount of 5 weight percent, guar gum in the amount of 0.5 weight percent, carboxy methylcellulose in the amount of 0.5 weight percent, sodium saccharin in the amount of 0.5 weight percent, xylitol in the amount of 5.0 weight percent, collagen in the amount of 2.0 weight percent, sodium benzoate in the amount of 0.3 weight percent, precipitated silica in the form of zeodent 165 in the amount of 5.0 weight percent, sparkle glitter in the amount of 1.2 weight percent, and trace amounts of flavor to taste, and sodium bicarbonate in an amount sufficient bring and buffer the composition to a pH value of at least 8.

The Zeodent® products are precipitated silicas with low surface area and enhanced flavor compatibility. Discussed in U.S. Pat. No. 6,946,119 to Gallis et al, Zeodent® products are used in some dentifrices for their antimicrobial activity.

This invention also comprises a group of products designed for protecting the oral health of babies, infants, and children. These products include antimicrobial and remineralization oral health care products with a pH that is alkaline for the protection of the oral cavity of youngsters comprising suckers and other hard candies, popsicles, rinses, gel, wipes, varnishes and swabs.

More specifically, the product is an antimicrobial wipes which are pre-moistened with a solution comprising fluoride and xylitol, and a pH value of about 8. Furthermore, the solution for said wipe comprises 63 weight percent water, 10 weight percent glycerin, 25 weight percent xylitol, 2 percent sodium benzoate, flavor, and sufficient sodium bicarbonate to bring and buffer the pH of the wipe to a value of at least 8.

The solution is pre-applied to a small (preferably 5"×3", although the size may vary) non-woven cotton fabric as a pre-moistened wipe for application and cleansing of a child's oral cavity, teeth, tongue, and gums. The wipe is used twice daily, especially after mealtimes.

The oral health product contains propylene glycol, polyethylene glycol, hydrogenated castor oil, aloe vera, sunflower oil, avocado oil, glycerin or flax seed oil can be optionally added in quantities less than 10% to increase oral moisturization.

Being able to document successful treatment outcomes provides validation for both the patient and his/her dental team that the medical model of caries diagnosis and treatment is effective. The products of this invention provide patients and the dental team with confidence that the bacterial infection can and is being controlled. With annual screenings, potential problems can be identified and addressed before serious restorative intervention is required.

The methods of this invention include a method for providing oral antimicrobial treatment and remineralization of the teeth of a patient comprising the steps of diagnosing and treating dental caries from a medical model comprising the steps of
  a) analyzing the biofilm in a patient's mouth;
  b) measuring the bacterial load in the mouth using ATP as an indication of the patient's oral bacterial load;
  c) correlating the ATP bioluminescence level of the oral biofilm in a mouth at rest and the number of CFU's of cariogenic bacteria present in the mouth;
  d) prescribing a regimen of products that are effective against a bacterial biofilm selected from the group consisting of heat, mechanical debridement and a strong oxidizing agent;
  e) providing antimicrobial and remineralization oral health care products with a pH that is alkaline ranging from about 8 to about 11.5 and pH buffers to maintain these pH levels for the maintenance and reformation of healthy bacteria in the biofilm;
  f) monitoring the patient until the biofilm is maintained in a healthy state.

In this manner, the oral health care products are selected from the group consisting of rinses including a maintenance rinse, a two-component treatment rinse, oral sprays, toothpastes, gels, varnishes, creams, chewing gums, mints, and floss.

The oral care antimicrobial/remineralization products of this invention have a pH in the range between about 8.0 and 11.5 as well as pH buffers to maintain these pH levels.

More specifically, a maintenance rinse of this invention comprises about 73 weight percent water, about 25 percent xylitol, about 1 weight percent sodium benzoate, about 1 percent potassium sorbate, 0.05 percent sodium fluoride, 0.2 percent flavor, 0.2 percent polysorbate 20, sodium bicarbonate or sodium hydroxide to boost pH to above 8.0, and trace amounts of 90% polyphenol and cranberry extract.

Furthermore, the therapeutic rinse is a two-part rinse that is utilized for two weeks wherein a single dose of the two part rinse is mixed each time it is used. The two-part treatment rinse is used for two weeks by the patient by swishing the rinse in his/her mouth for a minute and expectorating. The first part of the treatment rinse that comprises water in the amount of about 73 weight percent, xylitol in the amount of 22 weight percent, sodium benzoate in the amount of 2.0 weight percent, sodium fluoride in the amount of 0.05 weight percent, mint oil in the amount of 1.0 weight percent, poloxamer in the amount of 1.25 weight percent, menthol in the amount of 1.0 weight percent, and the second part comprises water in the amount of about 92 weight percent, sodium hydroxide in a quantity to buffer the pH of the second component to 11.9, and 5% sodium hypochlorite solution in the amount of 8 percent to bring the total sodium hypochlorite concentration to 0.4 percent.

After two weeks of the treatment rinse, the patient is then placed on daily use of the maintenance rinse. The rinses, along with the other products of this invention, assure that elevated pH plays a major role in the re-establishment of a healthy, normal biofilm in the patient's mouth.

Scope of the Invention

The invention claimed is:

1. A method of treating biofilm disease including the steps of
 (a) preparing a two-part therapeutic rinse comprising a first part and second part that are separated and in amounts that upon mixing provide a single dose each time the rinse is used,
 said first part comprising water and a fluoride and
 said second part consisting of an aqueous solution of an oxidizing agent selected from the group consisting of sodium hypochlorite, calcium hypochlorite, potassium hypochlorite, and magnesium hypochlorite, and
 (b) mixing said first and second parts to provide said single dose each time the rinse is used, and
 (c) rinsing a patient's mouth with said single dose and expectorating.

2. A method of treating biofilm disease including the steps of
 (a) preparing a two-part therapeutic rinse comprising a first part and second part that are separated and in amounts that upon mixing provide a single dose each time the rinse is used,
 said first part comprising water, xylitol, and a fluoride and
 said second part consisting of a buffered solution at an alkaline pH effective to drive the pH of a patient's oral biofilm to above at least a value of 7.0 and an oxidizing agent selected from the group consisting of sodium hypochlorite, calcium hypochlorite, potassium hypochlorite, and magnesium hypochlorite,
 (b) mixing said first and second parts to provide said single dose each time the rinse is used, and
 (c) rinsing a patient's mouth with said single dose for a minute and then expectorating, and
 (d) using the rinse over a two weeks and then followed by a maintenance rinse.

3. The method of claim 2 where the first part consists of about
 73 weight percent water,
 22 weight percent xylitol,
 0.05 weight percent sodium fluoride, and
 the second part comprises about 92 weight percent water and an 8 weight percent sodium hypochlorite solution.

4. The method of claim 3 where, upon mixing the first and second parts into the single dose, the concentration of the sodium hypochlorite solution is about 0.4 weight percent.

* * * * *